United States Patent
Longo et al.

(10) Patent No.: US 7,854,939 B2
(45) Date of Patent: Dec. 21, 2010

(54) GEL USEFUL FOR THE DELIVERY OF COSMETIC ACTIVE INGREDIENTS

(75) Inventors: Antonio Longo, Rome (IT); Mose Santaniello, Nettune (IT); Paola Risi, Sermoneta (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 91 days.

(21) Appl. No.: 11/938,001

(22) Filed: Nov. 9, 2007

(65) Prior Publication Data

US 2008/0279900 A1 Nov. 13, 2008

(30) Foreign Application Priority Data

May 11, 2007 (EP) ............... PCT/EP2007/054574

(51) Int. Cl.
*A61K 8/02* (2006.01)
*A61K 9/14* (2006.01)

(52) U.S. Cl. ............ 424/401; 424/489; 424/497; 424/59; 424/60; 424/444; 424/451; 424/463; 424/455; 424/498; 514/547; 514/561; 514/170; 562/567

(58) Field of Classification Search ............... 424/401, 424/497, 489, 59, 60, 444, 541, 463, 455, 424/498; 514/547, 561, 152; 560/170; 562/567
See application file for complete search history.

(56) References Cited

U.S. PATENT DOCUMENTS

| 6,149,924 A * | 11/2000 | Paul ..................... 424/401 |
| 6,703,042 B1 * | 3/2004 | Buononato ............ 424/444 |
| 2004/0170585 A1 * | 9/2004 | Berens et al. ............ 424/62 |

\* cited by examiner

*Primary Examiner*—Ardin Marschel
*Assistant Examiner*—Savitha Rao
(74) *Attorney, Agent, or Firm*—Lucas & Mercanti, LLP

(57) ABSTRACT

A gel, for cosmetic use, composed of a mixture of a polymer which forms a gel, a surfactant, and propionyl L-carnitine glycinate hydrochloride, useful for treating disturbances of the skin such as cellulite and wrinkles is described.

4 Claims, 1 Drawing Sheet

GEL USEFUL FOR THE DELIVERY OF COSMETIC ACTIVE INGREDIENTS

CROSS-REFERENCE TO RELATED APPLICATIONS

Figure 1:
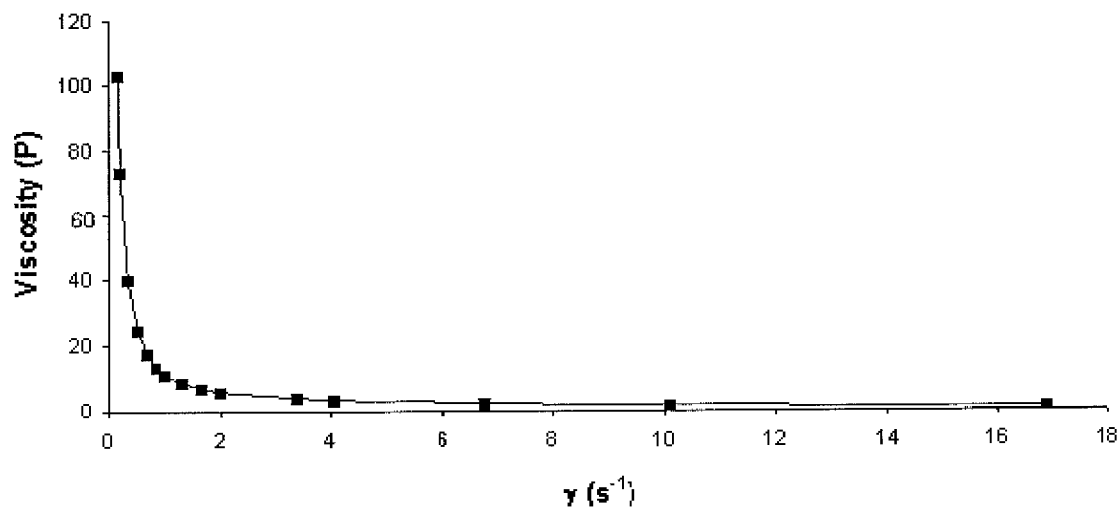

This application claims the benefit of priority from PCT International application No. PCT/EP2007/054574 filed May 11, 2007, the contents of which are incorporated herein by reference.

The present invention relates to a cosmetic composition, topically administrable, in the form of a solid powder, which comprises a mixture of: a polymer which forms a gel; a surfactant and one or more active ingredients useful for treating disturbances of the skin, in which said powder once is reconstituted with a suitable amount of water, or a liquid solution, provides a gel useful for preventing or treating said disturbances of the skin.

The present invention further relates to a cosmetic use of a salt of L-carnitine or an alkanoyl L-carnitine with amino acids having formula (I):

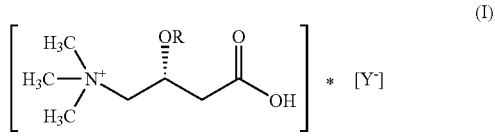

in which:

R is hydrogen or a straight or branched-chain alkanoyl group having 2-5 carbon atoms selected from the group consisting of acetyl, propionyl, butyryl, valeryl and isovaleryl;

Y is the anion of an amino acid occurring in proteins selected from the group consisting of: leucine, isoleucine, valine, cysteine, arginine, glutamic acid, glutamine, asparagine, glycine, alanine, threonine, serine, proline, hystidine, methionine, phenylalanine and tryptophane;

the anion Y$^-$ can optionally be salified at the amino group, preferably with a hydrohalogen acid such as hydrochloric acid or phosphoric acid;

The salts of L-carnitine or an alkanoyl L-carnitine with amino acids of formula (I) are useful agents for preparing a cosmetic composition topically administrable for supporting the fibrous matrix layer of tissue beneath the skin; for preventing subdermal tissue from entering or protruding into to the dermis; for treating patients having cellulite, or for the purpose of causing the contraction of laxed or wrinkled tissues below the surface of the epidermis.

FIELD OF THE INVENTION

The distribution of adipose tissue throughout the body is not uniform. In certain portions of the body it is present in great abundance such as in the subcutaneous tissue. A distinction must be made between fat and adipose tissue; the latter being a distinct tissue, the former an oily substance. Adipose tissue consists of small vesicles referred to hereinafter as "fat cells" lodged within the matrix of areolar connective tissue. Fat cells vary greatly in size; having an approximate diameter of about 0.05 mm. They are formed of a delicate protoplasmic membrane filled with the oily substance which is liquid during life but solidifies after death. These fat cells are contained in discrete clusters in the areolae of fine connective tissue.

Areolar tissue is a form of connective tissue wherein the investing connective tissue matrix is separated into areolae or spaces which open into one another and are easily permeated by fluids. Areolar tissue binds different parts of the body together. The elasticity of areolar tissue and the permeability of its areolae allows the various parts of the body to move relative to one another. Most particularly, areolar connective tissue is found beneath the skin in a continuous layer all over the body, connecting the skin (dermis) to subjacent tissues. In many parts the areolae are occupied by fat cells; the matrix and fat cells constituting adipose tissue which is referred to alternatively herein as "depot fat".

Cellulite is typically characterized by dermal deterioration due to a breakdown in blood vessel integrity and a loss of capillary networks in the dermal and subdermal levels of the skin. The vascular deterioration tends to decrease the dermal metabolism. This decreased metabolism hinders protein synthesis and repair processes, which results in dermal thinning. The condition is further characterized by fat cells becoming engorged with lipids, swelling, and clumping together, as well as excess fluid retention in the dermal and subdermal regions of the skin. Thus, individuals afflicted with cellulite tend to have a thicker subcutaneous fatty layer of skin. In the advanced stages of cellulite, reticular protein deposits called septa begin to form around the fatty deposits in the skin and occlude the fat cells. As the condition further progresses, hard nodules of fat cells and clumps of fat surrounded by septa form in the dermal region. This leads to the surface of the skin displaying considerable heterogeneity and being characterized as having a "cottage cheese" appearance. This appearance is most pronounced in overweight individuals. Individuals with cellulite also tend to have a thinner epidermis and dermis in the affected region, decreased firmness of the skin, and decreased rate of cell renewal.

There is no quick fix solution for cellulite reduction, and the obvious and most inexpensive way to treat cellulite is to watch what we eat and drink, and burn those calories by exercising on a regular basis.

Thousands of OTC potions, creams and pills to combat cellulite have flooded the market but the fact remains that cellulite is still stubborn and refuses to budge easily.

The appearance of cellulite currently tends to be treated by administering xanthines, which include caffeine, theophylline, and aminophylline. Xanthines acts as a diuretic that removes water from the fat cells and thus reduces the size of the fat cells. The effect of xanthines, however, is temporary and the fat cells become rehydrated as soon as the individual replenishes the lost water.

A variety of vitamins and minerals have individually been administered to treat certain skin and other problems that occur when the patient has a deficiency of that vitamin or mineral. Vitamin A, for example, assists in the treatment of acne and to facilitate wound healing; vitamin C (ascorbic acid) assists in the prevention of skin bruising and wound healing; vitamin E is an antioxidant; and copper assists in the treatment of elastic tissue defects. [Neldner, K. H., Amer. Acad. Derm. Annl. Mtg., Wash. D.C., Dec. 6, 1993]. Topical use of vitamin C is also believed to ward off sun damage, reduce breakdown of connective tissues, and possibly promote collagen synthesis. [Dial, W., Medical World News, p. 12, March 1991]. Vitamin E is used topically as an anti-inflammatory agent for enhancement of skin moisturization, for UV-ray protection of cells, and for retardation of premature skin aging.

It is known that preservatives are added to cosmetics composition to prevent the growth of microorganisms (eg, bacteria and fungi), which can spoil the product and possibly harm the user. It is also known that said preservatives are irritant for the skin.

In fact, "U. S. Food and Drug Administration, FDA Consumer, November 1991; revised May 1995" reports that according to a study of cosmetic reactions conducted by the North American Contact Dermatitis Group, preservatives are the second most common cause of allergic and irritant reactions to cosmetics. FDA also reports that in 1994 received approximately 200 reports of adverse reactions to cosmetics; skin-care products and makeup accounted for about 65; most of the 65 reports were either allergic reactions or skin irritations.

In "Nutrition Health Review, Fall, 1990" and in "In Contact Dermatitis; July, 1987; 17(1):26-34" is reported that a preservative for cosmetics "Kathon" is a major cause of cosmetic allergy.

In Dermatol. Nurs. 2006; 18(2):130-136, is reported that formaldehyde-releasing preservatives [the five most commonly used chemicals in this category are quaternium-15, dimethyl-dimethyl (DMDM) hydantoin, imidazolidinyl urea, diazolidinyl urea, and 2-bromo-2-nitropropane-1,3-diol (bronopol)], useful for preventing growth of gram-negative bacteria in cosmetics product cause localized allergic reactions and eruptions.

In spite of the large number of products useful for treating skin disturbances, in cosmetic field it is still a perceived need to have new vehicles and new active ingredients, useful for preparing cosmetic compositions for the preventing or treating skin disturbances, which do not show the drawbacks of the products known in the art.

DETAILED DESCRIPTION OF THE INVENTION

It has now been found that a solid powder, which comprises a mixture of a natural or synthetic polymer which forms a gel, a surfactant, and one or more active ingredients useful for the prevention or treatment of disturbances of the skin; once is reconstituted with a solution provides a gel suitable for cosmetic use.

The powder according to the present invention, respect to the gel or cosmetic compositions present on the market, presents the following advantages:

(a) is useful for preparing composition for the delivery of cosmetic active ingredients which are not stable in solution;

(b) may not contain irritant preservatives;

(c) is useful for preparing extemporaneous liquid or semi liquid composition to be directly applied to the skin [as a mono-dose or a dose for a day (or more) application].

It is therefore an object of the present invention a solid powder which comprises:

a) a natural or synthetic polymers which forms a gel, an example of said polymer is a carboxy vinyl polymer such as Carbopol;

b) a suitable surfactant selected from: sodium dodecyl sulphate; amino acid based cationic surfactant made from, for example, L-arginine, DL-pyrrolidone carboxylic acid, coconut fatty acids; or amino acid-based nonionic surfactants; and c) at least one active ingredient useful for the prevention or treatment of disturbances of the skin selected from:

agents supporting the microcirculation which include, but are not limited to, extracts of Gingko biloba, ruscus, melilot, red vine, viburnum;

agents for the activation of the lipolysis which include, but are not limited to, extracts of Ground ivy (Glechoma), root of Angelica, extract of Paulinia, Subdued or of the xanthic bases such as caffeine, theobromine and theophylline;

anti-inflammatory compounds which include, but are not limited to, rosmarinic acid, glycyrrizinate derivatives, alpha bisabolol, azulene and derivatives thereof, asiaticoside, sericoside, ruscogenin, escin, escolin, quercetin, rutin, betulinic acid and derivatives thereof, catechin and derivatives thereof;

skin whitening compounds which include, but are not limited to, ferulic acid, hydroquinone, arbutine, and kojic acid;

antioxidants and anti-wrinkling compounds which include, but are not limited to, retinol and derivatives, tocopherol and derivatives, salicylates and their derivatives;

agents which improve skin penetration and efficacy of common anticellulite agents which include, but are not limited to a monocarboxylic acids comprising lactic acid, glycolic acid, mandelic acid and mixtures thereof;

essential fatty acids (EFAs) exerting an important role in skin defense against oxidative stress, by entering in the lipid biosynthesis of epidermis and providing lipids for the barrier formation of the epidermis; preferred essential fatty acids are selected from the group consisting of linoleic acid, gamma-linolenic acid, homo-gamma-linolenic acid, columbinic acid, eicosa-(n-6,9,13)-trienoic acid, arachidonic acid, gamma-linolenic acid, timnodonic acid, hexaenoic acid and mixtures thereof;

sunscreens, for example, derivatives of Para Amino Benzoic Acid (PABA), cinnamate and benzophenone derivatives such as octyl methoxy-cinnamate and 2-hydroxy-4-methoxy-benzophenone; or salts of L-carnitine or an alkanoyl L-carnitine with amino acids having formula (I):

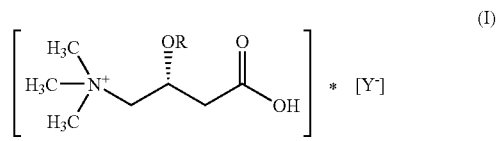

in which: R is hydrogen or a straight or branched-chain alkanoyl group having 2-5 carbon atoms selected from the group consisting of acetyl, propionyl, butyryl, valeryl and isovaleryl; and Y is the anion of an amino acid occurring in proteins selected from the group consisting of: leucine, isoleucine, vahine, cysteine, arginine, glutamic acid, glutamine, asparagine, glycine, alanine, threonine, serine, proline, hystidine, methionine, phenylalanine and tryptophane;

the anion $Y^-$ can optionally be salified at the amino group, preferably with a hydrohalogen acid such as hydrochloric acid or phosphoric acid;

preferred active ingredients are those which are not stable in water or in solution; most preferred is propionyl L-carnitine glycinate hydrochloride.

The powder according to the present invention once reconstituted with water or a solution, provides a gel suitable for cosmetic use.

It is a further object of the present invention a gel which comprises:

a) a natural or synthetic polymers which forms a gel, an example of said polymer is a carboxy vinyl polymer such as Carbopol;

b) a suitable surfactant selected from: sodium dodecyl sulphate; amino acid based cationic surfactant made from, for example, L-arginine, DL-pyrrolidone carboxylic acid, coconut fatty acids; or amino acid-based nonionic surfactants; and c) one or more active ingredients useful for the prevention or treatment of disturbances of the skin mentioned above.

It is a further object of the present invention a method of preparation of the powder of the invention which comprises the following steps:

a) preparation of the gel dissolving in water, or in a suitable solution, the gelling agent, the surfactant and one or more active ingredients mentioned above, maintaining the pH from 4.0 to 6.0; to control the pH suitable inorganic and/or organic basic compounds can be used; an example of inorganic basic compound is sodium or potassium hydroxide; an example of organic basic compounds is a basic aminoacid selected from lysine, arginine, histidine, or ornithine;

b) the gel so obtained is divided in single doses and put into vials;

c) to obtain a powder the vials of step b) are lyophilized; alternatively the gel of point a) is directly subjected to Spray-drying procedure and the powder so obtained is put, in a suitable amount, into vials.

The powder so obtained before the use needs to be reconstituted with a suitable amount of water, or a solution, to obtain the gel to be applied to the skin.

It is a further object of the present invention a cosmetic composition, comprising the powder or the gel mentioned above, and optionally at least one excipient or diluent selected from:

thickener agents in any suitable proportion well known to the skilled in the art; exemplary thickener agent are guns such as xanthan, carrageenan, gelatin, karaya, pectin and locust beans gum; said water-based cosmetic composition can be protected;

preservatives against the growth of microorganisms; suitable preservatives include alkyl esters of p-hydroxybenzoic acid, hydantoin derivatives, propionate salts, methyl paraben, propyl paraben, imidazolidinyl urea, sodium dehydroxyacetate benzyl alcohol, and a variety of quaternary ammonium compounds. Preservatives, if any, are added any suitable proportion well known to the skilled in the art;

silicone polymers in any suitable proportion well known to the skilled in the art;

emollients acting both as carrier, to facilitate the dispersion of the active ingredient and skin softeners; emollients may be incorporated in the cosmetic composition of the invention in any suitable proportion well known to the skilled in the art; suitable emollients may be classified under such general chemical categories as esters, fatty acids and alcohols, polyols and hydrocarbons; an example of fatty di-esters include: dibutyl adipate, diethyl sebacate, diisopropyl dimerate, propylene glycol myristyl ether acetate, diisopropyl adipate, and dioctyl succinate; an example of branched chain fatty esters include 2-ethyl-hexyl myristate, isopropyl stearate and isostearyl palmitate; an example of tribasic acid esters include triisopropyl trilinoleate, trilauryl citrate, tributirrine, and saturated or unsaturated vegetable oils; an example of straight chain fatty esters include lauryl palmitate, myristyl lactate, oleyl eurcate, stearyl oleate coco-caprylate/caprate, and cetyl octanoate; an example of fatty alcohols and acids are $C_{10}$-$C_{20}$ compounds such as cetyl, myristyl, palmitic and stearyl alcohols and acids; an example of polyols are linear and branched chain alkyl polyhydroxyl compounds, such as propylene and butylene glycol, sorbitol glycerin, as well as polymeric polyols such as polypropylene glycol and polyethylene glycol; an example of hydrocarbons are linear $C_{12}$-$C_{30}$ hydrocarbon chains such as mineral oil, petroleum jelly, squalene and isoparaffins;

water;

colouring agents, opacifiers;

perfumes.

It is a further object of the present invention a cosmetic composition comprising as active ingredient propionyl L-carnitine glycinate hydrochloride, and optionally a farther active ingredient and/or excipient mentioned above.

It is a further object of the present invention the use of the solid powder or the gel mentioned above, for preparing a cosmetic composition useful for the prevention or treatment of disturbances of the skin selected from cellulite and wrinkle.

It is a further object of the present invention the use of propionyl L-carnitine glycinate hydrochloride, for preparing a cosmetic composition useful for the prevention or treatment of disturbances of the skin selected from cellulite and wrinkle.

According to another of its aspects the present invention relates to a kit for the topical administration of propionyl L-carnitine glycinate hydrochloride, optionally comprising one or more active ingredients, and/or one or more suitable diluents, and/or one or more excipients.

Further object of the present invention is a kit comprising the powder of the invention in admixture with one or more active ingredients (useful in the cosmetic field) and, separately, in the same or in a different container/vial, water or a liquid solution suitable for obtaining the gel of the invention.

A further object of the present invention is a kit comprising the powder of the invention, in which the active ingredient is propionyl L-carnitine glycinate hydrochloride, and separately, in the same or in a different container, water or a liquid solution.

A further object of the present invention is a kit comprising:

a) the powder of the invention (not mixed with a compound useful for cosmetic use);

b) one or more active ingredient useful for cosmetic use (in liquid, solid, cream, gel or powder form); and c) water or a liquid solution suitable for obtaining the gel of the invention; in which the (three) ingredients are into the same container/vial in separate space, and said (three) components can be easily mixed together to obtain the gel of the invention which may be directly topically administered.

The expert, or indeed any artisan of ordinary skill in container for cosmetic use can easily suggest suitable containers which contains, for example, the gel mixed with one or more drugs; or a powder and separately (in the same container) a liquid; or 2 or more different powders and a liquid; for single or multiple applications. Different containers/vials are also included in the present invention.

In yet another aspect of the invention there are provided methods of preventing or treating disturbances of the skin. These methods include topically administering an effective amount of the cosmetic composition such as those described herein to an area of the skin requiring such treatment. For purposes of the present invention, it is to be understood that "disturbances of the skin" include any of the myriad dermatological conditions, including those generally thought of as being cosmetic rather than medical, described herein or which those of ordinary skill foresee as benefiting from the application and or treatment of the compositions described herein.

According to the present invention propionyl L-carnitine glycinate hydrochloride in the form of cosmetic composition is administered topically, in the form of cream or lotion, comprising from 0.5 to 45% by weight, preferably from 5 to 35% by weight, more preferably from 10 to 25% by weight of active ingredient, optionally in admixture with suitable customary auxiliary agents. The preferred dose is 20%.

According to the present invention propionyl L-carnitine glycinate hydrochloride, in the form of cosmetic composition, is administered topically in the form of gel, or powder to be reconstituted with water or a liquid solution, comprising from 0.5 to 35% by weight, preferably from 5 to 25% by weight, more preferably from 7.5 to 15% by weight of active ingredient, optionally in admixture with suitable customary auxiliary agents.

The topical skin treatment composition of the invention can be formulated in all the forms topics used in beauty care: lotion, fluid cream, cream or gel. The composition can be packaged in a suitable container according to its viscosity and to the intended use by the user. For example, a lotion or fluid cream can be packaged in a bottle, in a roll-ball applicator, in a capsule, patch, in a propellant-driven aerosol device or a container fitted with a pump suitable for finger operation.

When the composition is a cream, it can simply be stored in a non-deformable bottle or in a squeeze container, such as a tube or a lidded jar.

For each particular form, one has recourse to suitable excipients.

These excipients must have all usually required qualities. As examples, one can quote: the propylene glycol, the glycerin, cetyl alcohol, the polyols, the phospholipids put in liposomes or not, oils vegetated, animal, mineral, preservatives, the dampeners, the thickeners, stabilizing and emulsifying usually used.

The expression "cosmetically acceptable ingredients" according to the present invention are products which are suitable for their use in cosmetic treatments, for example those included in the INCI list drawn by the European Cosmetic Toiletry and Perfumery Association (COLIPA) and issued in 96/335/EC "Annex to Commission Decision of 8 May 1996".

DISCUSSION OF THE DRAWINGS

FIG. 1 describes the behaviour of the gel of example 1 which is obtained adding 17.5 mL of water to 3 gr of the solid of example 1. In this figure it is shown that the viscosity decreases increasing the deformation velocity γ (shear rates) typical non-Newtonian flow behaviour.

Figure 2:
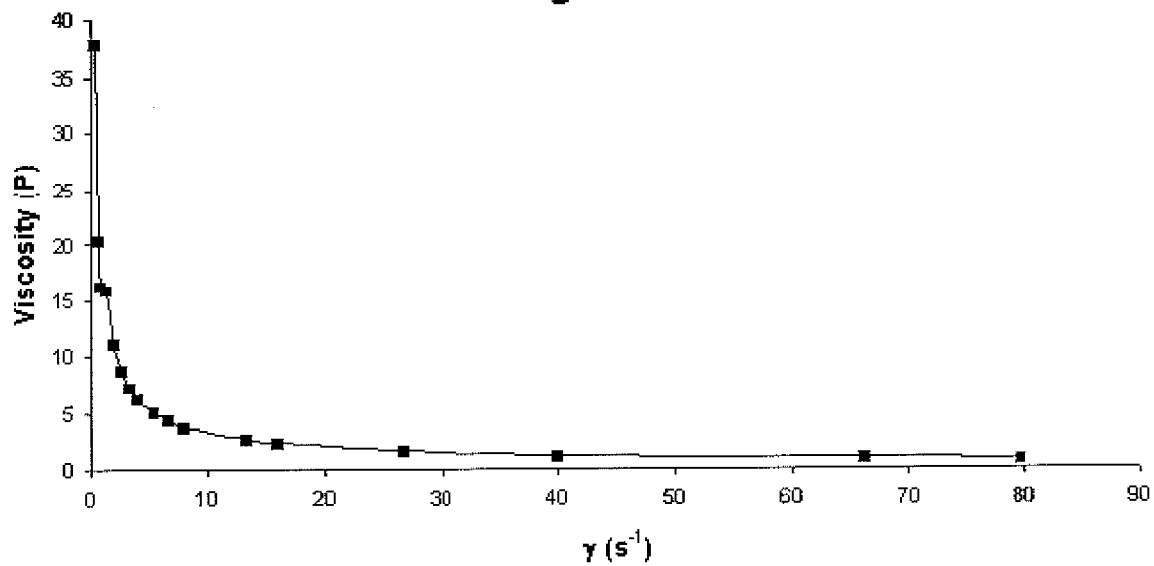

FIG. 2 describes the behaviour of the gel of example 2 which is obtained adding 10 mL of water to 1.7 gr of the solid of example 2. Also in this case the viscosity decreases increasing the deformation velocity γ (shear rates) typical non-Newtonian flow behaviour.

The following not limiting examples further illustrate the present invention.

Materials

Carbopol 974P NF (Noveon) and all other chemicals were purchased from Sigma and were used as received.

Preparation of the "Gel Base"

7.5 g of Carbopol 974P (Noveon) were slowly added to 500 mL of water. The mixture so obtained was kept under stirring at room temperature for 18 h.

A gel was obtained.

EXAMPLE 1

400 mg of sodium dodecyl sulfate (SDS) were added to 42.4 gr of gel base; the mixture so obtained was kept under stirring till complete solubilization of SDS. 5.03 gr of propionyl L-carnitine glycinate hydrochloride (PLCGH) were slowly added and the gel mixture was kept under stirring (about 30 min) till complete solubilization. 2.25 gr of L-lysine were added and the gel was kept under stirring for about 2 hours (pH 4-6, preferred 4.5-5). The gel was diluted with 100 ml of water, kept under stirring for about 10 minutes, and lyophilized for 18 hours.

A white solid was obtained.

Adding 5 mL of water to 1 gr of the white solid, a gel containing 10% of propionyl L-carnitine hydrochloride was readily obtained.

EXAMPLE 2

1.6 gr of SDS were added to 169.5 gr of the gel base; the gel mixture so obtained was kept under stirring till complete solubilization.

20 gr of propionyl L-carnitine glycinate hydrochloride were slowly added to the gel and the mixture was kept under stirring till complete solubilization.

9 gr of L-lysine were added, the gel mixture so obtained (pH 4.5-5) was kept under stirring for about 2 hours.

The gel was diluted with 300 ml of water, and the viscous solution, constantly kept under stirring was concentrated through a Spray-drying (Buchi B-191) under the following conditions: Inlet=70° C., ASP=85%, Pump=0.03.

A white solid was obtained.

Adding 5 mL of water to 1 gr of the white solid, a gel containing 10% of propionyl L-carnitine hydrochloride was readily obtained.

Reological Studies

The reological studies were carried out with a rotational viscometer of the concentric cylinder type (Viscometer TV-10 Toky Sangyo equipped with a small sample adapter and rotor type M3). The viscosity of the samples were measured at various rates at 25° C. The temperature was maintained within +/−0.1° C. by a recirculating bath connected to the viscometer. The samples were equilibrated for five minutes to reach the running temperature prior to each measurement.

The results obtained, using the gel of the Examples 1 and 2, are reported in FIGS. 1 and 2 respectively.

EXAMPLE 3

Topical Anticellulite Activity of Propionyl L-Carnitine Glycinate Hydrochloride

The effectiveness of a topically administered product according to the invention was tested for its ability to reduce the appearance of cellulite in the thigh area. A total of twenty-two (22) female subjects ranging in age from 28 to 60 years of age were selected to evaluate the composition of the invention.

The subjects were selected based on their cellulite intensity in the thigh area having a bi-lateral symmetry. Subjects with grades 1 and 2 cellulite were chosen, as a 5-point grading scale was used to rate the cellulite severity of each subject. The scale ranged from 0 to 4, being 0=No cellulite; 1=Small bumps or depressions; 2=Striations and bumps; 3=Pronounced lumpiness of the skin and striations; 4=All of the above plus hard sub-surface nodules.

All subjects had the absence of any visible skin disease(s) which might be confused with a skin reaction from the test material were in general good health with no known allergies, especially to cosmetic or toiletry products; had no evidence of acute or chronic disease; were not pregnant or lactating, were not on any diet or weight reduction program; and were not on any regular exercise program (immediately prior to or during the course of the study).

At baseline each subject received a visual examination conducted by a qualified technician.

Subjects were treated on the right thigh and the left thigh was considered as a "control".

The test sites were carefully demarcated to ensure subsequent evaluations were made on the same test areas.

The test sites were examined by a trained observers and scored for the degree of cellulite at each clinic visit according to the following scale: 0=No visible cellulite; 1=Very little visible cellulite, no dimpling; 2=Visible cellulite, evidence of shallow dimpling; 3=Easily visible cellulite, moderate to pronounced dimpling; 4=Extremely visible cellulite, heavy and deep dimpling.

The subject were taught to carried out the application using the gel of Example 1, two times a day at morning and at night, for 6 weeks.

Subjects were provided with a three (3) week supply of the test product for use at home and were instructed to discontinue the use of their normal anti-cellulite products, to avoid introducing any new products for treating cellulite during the study, and to not be on any diet or weight reduction program or on any regular exercise program immediately prior to or during the course of the study. Each subject was also instructed to keep a diary to document compliance. After three weeks of product usage, the subjects returned to the laboratory for a visual evaluation of the test sites.

Another three (3) week supply of the test product and a new diary was then dispensed to each subject. After the second three (3) weeks of product usage (week 6) the subjects returned to the laboratory for a final visual evaluation.

The cellulite evaluation was made according the method described in Cosmetics & Toiletries, 61-70, June 1995, by comparison of the right thigh versus left thigh.

During the treatment period none of the subject reported adverse events such as itching and/or redness.

Results obtained are reported in Table 1.

TABLE 1

Change of the cellulite condition after 6 weeks application

| Condition | Gel of Example 1 |
| --- | --- |
| Thigh diameter | −10% |
| Fatty layer thickness | −26% |
| Skin firmness | +18% |
| Skin hydration | +26% |
| Surface smoothness | +40% |
| Subjective improvement | +55% |
| Clinical grading | +33% |
| Irritation reactions | 0 |

The results above show that the composition containing propionyl L-carnitine glycinate hydrochloride effectively ameliorate the cellulite condition.

The use of the gel base containing the same amount of L-lysine and glycine present in the gel obtained using the powder of example 1, in which the pH was adjusted to 4.5-5 (without propionyl L-carnitine glycinate hydrochloride) did not show any improvement of the cellulite condition (data not shown).

EXAMPLE 4

Topical Application of Propionyl L-Carnitine Glycinate Hydrochloride for Reducing Appearance of Wrinkles Twelve people participated as subjects in a test of the gel. Each subject was told it was to be used on the wrinkles around his/her eyes and that the protocol was to be a one-part application. A technician was assigned the task of measuring the wrinkles on the faces of the subjects before and after application of the gel of the invention. This technician drew two ovals on a piece of paper. A quick representative drawing was made of the subject's wrinkles and fine lines.

The gel of Example 1 was then applied to the right eye area, two times a day, at morning and at night, during 7 days treatment. At the end of a week treatment, five minutes after the last application of the gel, a second drawing of the skin's appearance was made.

The gel produced a noticeable change in the skin's appearance.

The use of the gel base containing the same amount of L-lysine and glycine present in the gel obtained using the powder of example 1, in which the pH was adjusted to 4.5-5 (without propionyl L-carnitine glycinate hydrochloride) did not show any improvement of the skin's appearance.

No adverse effect were reported by the subjects treated.

The results reported in Examples 3 and 4 indicate that use of compound of the invention is useful for the prevention treatment of cellulite and wrinkle, the observed degree of improvement is a function of the length of treatment as indicated above. This strongly suggests the treatment has imparted an improved skin infrastructure by beneficially affecting the dermis of the skin.

Noveon, Inc. introduced Carbopol® polymer to the cosmetic industry in the middle 1950's.

The salts of L-carnitine or an alkanoyl L-carnitine with amino acids having formula (I) are known compounds and their reparation process is described in U.S. Pat. No. 6,703,042.

The topical use of the salts of L-carnitine or an alkanoyl L-carnitine with amino acids having formula (I) for preventing or treating cellulite was never disclosed before.

The cosmetic compositions according to the present invention are composed of active ingredients which are familiar to operators in the cosmetic field, already in use and their toxicological profiles already known.

Their procurement therefore is very easy, inasmuch as these are products which have been on the market now for a long time and are of a grade suitable for human administration.

The invention claimed is:

1. A cosmetic composition comprising an active ingredient, wherein the active ingredient is propionyl L-carnitine glycinate hydrochloride.

2. The composition of claim 1, further comprising, one or more cosmetically acceptable excipients and/or diluents.

3. The composition of claim 1 in a lyophilized form.

4. The composition of claim 1 in a gel form.

* * * * *